(12) United States Patent
Armstrong

(10) Patent No.: US 6,350,611 B1
(45) Date of Patent: Feb. 26, 2002

(54) TRANSCRIPTIONAL REGULATORY REGION

(75) Inventor: Katherine Armstrong, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 09/239,706

(22) Filed: Jan. 28, 1999

Related U.S. Application Data

(60) Provisional application No. 60/072,944, filed on Jan. 29, 1998.

(51) Int. Cl.$^7$ .............................. C12N 5/04; C12N 15/82
(52) U.S. Cl. ................................... 435/320.1; 536/24.1
(58) Field of Search .............................. 435/69.1, 320.1, 435/410, 412, 419, 430, 430.1, 468, 470; 536/24.1, 23.7, 23.6; 800/278, 295, 298, 314, 320.1, 320.2

(56) References Cited

PUBLICATIONS

Hess et al, Plant Sci., vol. 72, pp. 233–244, 1990.*
Stewart, J. McD., Integrated Events In The Flower and Fruit, in Cotton Physiology (J.R. Mauney and J. McD. Stewart, eds.), pp. 261–272, 1986.*
Frame et al, Plant J., vol. 6, pp. 941–948, 1994.*
Kuehnle et al, Plant Cell Rep., vol. 11, pp. 484–488, 1992.*
Firoozabady et al, Plant Mol. Biol., vol. 10, pp. 105–116, 1987.*
Ishida et al, Nature Biotech., vol. 14, pp. 745–750, 1996.*

* cited by examiner

*Primary Examiner*—Amy J. Nelson
*Assistant Examiner*—Ashwin Mehta
(74) *Attorney, Agent, or Firm*—Donald R. Stuart

(57) ABSTRACT

Plant cell aggregates and plant tissues can be transformed by elongated, needle-like structures called "whiskers". The process comprises the agitation of plant cell aggregates and plant tissues of the plant to be transformed in the presence of DNA and whiskers, whereby DNA uptake and integration thereof is facilitated. The process may be applicable to other plant cell aggregates and plant tissues which have not proven easily transformable by other techniques.

2 Claims, No Drawings

TRANSCRIPTIONAL REGULATORY REGION

This application claims benefit of U.S. Provisional application serial No. 06/072,944, filed Jan. 29, 1998.

FIELD OF INVENTION

This invention relates to a method of using elongated, needle-like microfibers or "whiskers" to transform plant cell aggregates and selected plant tissues.

BACKGROUND OF THE INVENTION

Until recently, genetically manipulated plants were limited almost exclusively to those events created by application of classical breeding methods. Creation of new plant varieties by breeding was reserved primarily for the most agronomically important crops, such as corn, due to the cost and time needed to identify, cross, and stably fix a gene in the genome, thus creating the desired trait. In comparison, the advent of genetic engineering has resulted in the introduction of many different heterologous genes and subsequent traits into diverse crops including corn, cotton, soybeans, wheat, rice, sunflowers and canola in a more rapid manner. However, the intergression of a new transgene into elite germplasm is still quite a laborious task due to the tissue culturing and back-crossing needed to produce a commercially viable, elite, line.

Several techniques exist which allow for the introduction, plant regeneration, stable integration, and expression of foreign recombinant vectors containing heterologous genes of interest in plant cells. One such technique involves acceleration of microparticles coated with genetic material directly into plant cells (U.S. Pat. No. 4,945,050 to Cornell; U.S. Pat. No. 5,141,131 to DowElanco; and U.S. Pat. Nos. 5,538,877 and 5,538,880, both to Dekalb). This technique is commonly referred to as "microparticle bombardment" or "biolistics". Plants may also be transformed using Agrobacterium technology (U.S. Pat. No. 5,177,010 to University of Toledo, U.S. Pat. No. 5,104,310 to Texas A&M, European Patent Application 0131624B1, European Patent Applications 120516, 159418B1 and 176,112 to Schilperoot, U.S. Pat. Nos. 5,149,645, 5,469,976, 5,464,763 and 4,940,838 and 4,693,976 to Schilperoot, European Patent Applications 116718, 290799, 320500 all to Max Planck, European Patent Applications 604662,627752 and U.S. Pat. No. 5,591,616 to Japan Tobacco, European Patent Applications 0267159, and 0292435 and U.S. Pat. No. 5,231,019 all to Ciba-Geigy, U.S. Pat. Nos. 5,463,174 and 4,762,785 both to Calgene, and U.S. Pat. Nos. 5,004,863 and 5,159,135 both to Agracetus). Another transformation method involves the use of elongated needle-like microfibers or "whiskers" to transform cell suspension cultures (U.S. Pat. Nos. 5,302,523 and 5,464,765 both to Zeneca). In addition, electroporation technology has been used to transform plant cells from which fertile plants have been obtained (WO 87/06614 to Boyce Thompson Institute; U.S. Pat. Nos. 5,472,869 and 5,384,253 both to Dekalb; U.S. Pat. No. 5,679,558, 5,641,664, and WO9209696 and WO9321335 to Plant Genetic Systems).

Despite all of the technical achievements, genetic transformation and routine production of transgenic plants in a commercially viable, elite, germplasm is still a laborious task. For example, microparticle bombardment, while capable of being used either on individual cells, cell aggregates, or plant tissues, requires preparing DNA-attached gold particles and optimization of an expensive and not yet widely available, "gun" apparatus. Techniques involving Agrobacterium are extremely limited because not all plant species or varieties within a given species are susceptible to infection by the bacterium. Electroporation techniques are not preferred due to the extreme difficulties and cost typically encountered in routinely making protoplast from different plant species and tissues thereof and the concomitant low viability and low transformation rate associated therewith.

As disclosed herein, applicants have invented a method whereby plant cell aggregates and plant tissues from non-elite and elite germplasm can be directly and inexpensively transformed with a recombinant vector containing the gene of choice using whiskers. Applicants' invention is advantageous over currently used methods in that it is simple, quick and easy to use. Furthermore, applicants' invention is superior to that described in the art in that it eliminates the need to establish Type III callus cultures or establish and maintain cell suspension cultures, and can be used with either Type I or Type II callus, thus, is less germplasm limited. This means that applicants' invention, as described herein, can be used to transform elite genotypes directly thus eliminating the problems and time generally associated with gene intergression.

SUMMARY OF THE INVENTION

The present invention relates to the production of fertile, transgenic, Zea mays plants containing heterologous DNA preferably integrated into the chromosome of said plant and heritable by the progeny thereof.

One aspect of the present invention relates to Zea mays plants, plant parts, plant cells, plant cell aggregates, and seed derived from transgenic plants containing said heterologous DNA.

The present invention also relates to the production of fertile, transgenic, Oryza sativa L. plants containing heterologous DNA preferably integrated into the chromosome of said plant and heritable by the progeny thereof.

Another aspect of the present invention relates to Oryza sativa L. plants, plant parts, plant cells, plant cell aggregates, and seed derived from transgenic plants containing said heterologous DNA.

The present invention also relates to the production of fertile, transgenic, Gossypium hirsutum L. plants containing heterologous DNA preferably integrated into the chromosome of said plant and heritable by the progeny thereof.

Another aspect of the present invention relates to Gossypium hirsutum L. plants, plant parts, plant fibers, plant cells, plant cell aggregates, and seed derived from transgenic plants containing said heterologous DNA.

The invention further relates to a process for producing fertile transformed plants from Type I callus, Type II callus, hypocotyl-derived callus, or cotyledon-derived callus by whisker-mediated transformation.

The invention yet further relates to a process for producing fertile transformed plants from meristematic tissue by whisker-mediated transformation.

Another aspect of the invention relates to fertile, mature maize plants regenerated from Type I or Type II callus and transgenic seed produced therefrom.

Another aspect of the invention relates to fertile, mature rice plants regenerated from Type I callus and transgenic seed produced therefrom.

Yet, another aspect of the invention relates to fertile, mature cotton plants regenerated from hypocotyl-derived callus or cotyledon-derived callus and transgenic seed and fiber produced therefrom.

In a preferred embodiment, this invention produces the fertile transgenic plants described herein by means of whisker-mediated cell perforation and heterologous DNA uptake, said whisker-mediated cell perforation being performed on plant cell aggregates and plant tissues, followed by a controlled regimen for selection and production of transformed plant lines.

Other aspects, embodiments, advantages, and features of the present invention will become apparent from the following specification.

DETAILED DESCRIPTION OF THE INVENTION

The present invention relates to methods for production of fertile transgenic plants and seeds of, for example, the species Zea mays, Oryza sativa L., Gossypium hirsutum L., and Brassica napus by transforming plant cell aggregates and plant tissues of said species with the DNA construct of interest via whisker-mediated transformation. After transformation, transgenic plants are regenerated from said transformed plant cell aggregates and plant tissues and said regenerated plants express the chimeric DNA construct of interest. The transgenic plants produced herein by the methods described include: all species of corn including but not limited to field corn, popcorn, sweet corn, flint corn, dent corn and the like; all species of cotton; and all species of rice.

The following phrases and terms are defined below:

By "antisense" is meant an RNA transcript that comprises sequences complementary to a target RNA and/or mRNA or portions thereof and that blocks the expression of a target gene by interfering with the processing, transport, and/or translation of its primary transcript and/or mRNA. The complementarity may exist with any part gof the target RNA, i.e., the 5' non-coding sequence, 3'non-coding sequence, introns, or the coding sequence. Antisense RNA is typically a complement (mirror image) of the sense RNA.

By "cDNA" is meant DNA that is complementary to and derived from a mRNA.

By "chimeric DNA construction" is meant a recombinant DNA containing genes or portions thereof from one or more species in either the sense or antisense orientation.

By "constitutive promoter" is meant promoter elements that direct continuous gene expression in all cell types and at all times (i.e., actin, ubiquitin, CaMV 35S, 35T, and the like).

By "cosuppression" is meant the introduction of a foreign gene having substantial homology to an endogenous gene, and in a plant cell causes the reduction in activity of the foreign gene and/or the endogenous gene product. Cosuppression can be sometimes achieved by introducing into said plant cell either the promoter sequence, the 5' and/or 3' ends, introns or the coding region of a gene.

By "developmental specific" promoter is meant promoter elements responsible for gene expression at specific plant developmental stages, such as in early or late embryogenesis and the like.

By "enhancer" is meant nucleotide sequence elements which can stimulate promoter activity such as those from maize streak virus (MSV), alfalfa mosaic virus (AMV), alcohol dehydrogenase intron 1 and the like.

By "expression" as used herein, is meant the transcription of enzymatic nucleic acid molecules, mRNA, and/or the antisense RNA inside a plant cell. Expression of genes also involves transcription of the gene and may or may not involve translation of the mRNA into precursor or mature proteins.

By "foreign" or "heterologous gene" is meant a gene having a DNA sequence that is not normally found in the host cell, but is introduced by whisker-mediated transformation.

By "gene" is meant to include all genetic material involved in protein expression including chimeric DNA constructions, genes, plant genes and portions thereof.

By "genome" is meant genetic material contained in each cell of an organism and/or virus.

By "inducible promoter" is meant promoter elements which are responsible for expression of genes in response to a specific signal, such as: physical stimuli (heat shock genes); light (RUBP carboxylase); hormone (Em); metabolites, stress and the like.

By "modified plant" is meant a plant wherein the mRNA levels, protein levels or enzyme specific activity of a particular protein have been altered relative to that seen in an unmodified plant. Modification can be achieved by methods such as antisense, cosuppression, or over-expression.

By "plant cell aggregates", "plant cell lines", and "callus cell lines" is meant proliferating masses of tissue composed of a combination of undifferentiated and differentiated cells undergoing de novo morphogenesis and formed by placing a piece of plant material (explant) onto a growth-supporting medium under sterile conditions. The terms "plant cell aggregates", "plant cell lines", and "callus cell lines" are meant to include Type I and Type II callus cultures in monocotyledonous plants and hypocotyl- and cotyledon derived cultures in dicotyledonous plants. The terms defined herein are not intended to include either plant cell suspension cultures or Type III callus cultures.

By "plant tissues" is meant organized tissues including but not limited to meristems, embryos, pollen, cotyledons, germ cells, and the like.

By "promoter regulatory element" is meant nucleotide sequence elements within a nucleic acid fragment or gene which controls the expression of that nucleic acid fragment or gene. Promoter sequences provide the recognition for RNA polymerase and other transcriptional factors required for efficient transcription. Promoter regulatory elements from a variety of sources can be used efficiently in plant cells to express sense and antisense gene constructs. Promoter regulatory elements are also meant to include constitutive promoters, tissue-specific promoters, developmental-specific promoters, inducible promoters and the like. Promoter regulatory elements may also include certain enhancer sequence elements that improve transcriptional or translational efficiency.

By "tissue-specific" promoter is meant promoter elements responsible for gene expression in specific cell or tissue types, such as the leaves or seeds (i.e., zein, oleosin, napin, ACP, globulin and the like).

By "transgenic" is meant to include any Type I or Type II callus, hypocotyl- or cotyledon derived callus, tissue, plant parts or plants which contains heterologous DNA or a chimeric gene construct that was introduced into said callus, tissue, plant parts or plants by whiskers and was subsequently transferred to later generations by sexual or asexual cell crosses or cell divisions.

By "whiskers" is meant elongated needle-like bodies capable of being produced from numerous substances as described in "The Condensed Chemical Dictionary, Seventh Edition, Ed. Arthur & Elizabeth Rose, Reinhold Publishing Corp., New York (1966). The invention is not meant to be limited to the material from which the whiskers are made but instead is meant to define a needle-like shaped structure wherein said whisker is smaller than the cell for which it is intended to be used in the transformation thereof. It is within the scope of this invention for whiskers to be shaped in a manner whereby DNA entry into a cell is facilitated. It is also intended that the scope of said invention include any material having a needle-like shape, said needle-like shaped material being able to perforate a plant cell with or without cell walls and thus facilitate DNA uptake and plant cell transformation. It is also intended that the scope of this invention not include microinjection techniques, such as wherein a DNA molecule is inserted into a cell by passing said DNA through an orifice intrinsic to a needle, said needle being first inserted into said cell. Preferably, whiskers are metal or ceramic needle-like bodies, with those most preferred being made of either silicon carbide or silicon nitride and being 30×0.5 μm to 10×0.3 μm in size.

By "whisker-mediated transformation" is meant the facilitation of DNA insertion into plant cell aggregates and/or plant tissues by whiskers and expression of said DNA in either a transient or stable manner.

In producing plant cell lines, tissues of interest are aseptically isolated and placed onto solid initiation medium whereby processes associated with cell differentiation and specialization occurring in organized plant cell tissues are disrupted, thus resulting in said tissues becoming dedifferentiated. Typically, initiation medium is solidified by adding agar or the like because callus cannot be readily initiated in liquid medium. Media are typically based on the N6 salts of Chu et al., (1978, Proc. Symp. Plant Tissue Culture, Peking Press, p 43–56) being supplemented with sucrose, vitamins, minerals, amino acids, and in some cases, synthetic hormones. However, callus tissues can also proliferate on media derived from the MS salts of Murashige and Skoog, (1962 Physiol. Plant. 15: 473–497). Cultures are generally maintained in a dark, sterile environment at about 28° C.

Typically, plant cell lines are preferably derived from tissues found in juvenile leaf basal regions, immature tassels, hypocotyl tissue, and cotylendonary nodes. For maize and rice, plant cell lines which produce meristematic tissue can be used, with those from zygotic embryo tissue being most preferred. Tissues most preferred for producing said plant cell lines are isolated from developing maize ears 10 to 14 days after pollination and non-germinated rice seed. Hypocotyl and cotyledon-derived tissues from seedlings are most preferred for production of cotton plant cell lines.

After placing said tissues on solid medium, new meristems arise after several days to a few weeks from either the scutellar region, in the case of corn and rice, or from hypocotyl or cotyledonary tissue in the case of cotton. These new meristems produce undifferentiated parenchymatous cell aggregates without the structural order characteristic of the tissue from which they are derived. Plant cell aggregates lack any recognizable overall structure and contain only a limited number of the many different kinds of specialized cell types found in intact, organized plant tissues. Said aggregates have been classified into non-embryogenic and embryogenic depending on their regenerative capacity, mode of reproduction, and tissue morphology (Franz, 1988, Ph.D. Thesis, University of Wageningen, The Netherlands).

In corn and rice, non-embryogenic calli are comprised of soft, granular, translucent tissue consisting of elongated, vacuolated cells incapable of plant regeneration. Alternatively, embryogenic, monocotyledonous calli, being capable of somatic embryogenesis and plant regeneration, exist in three distinct morphotypes: Type I; Type II; and Type III.

Type I callus consists of compact, nodular, slow-growing embryogenic callus which proliferates as a mixture of complex tissues exhibiting shoot and/or scutellar-like structures (Phillips et al, 1988, In, Corn and Corn Improvement, pp 345–387). Said callus is characterized by a high degree of cellular differentiation, well developed vascular structures and has been referred to as compact embryogenic callus (U.S. Pat. No. 5,641,664 to Plant Genetic Systems). Essentially all monocotyledonous plants have tissue from which Type I callus can be produced. Plant regeneration in Type I callus normally occurs either through organogenesis by elongation of meristems (Green and Phillips, 1975, Crop Sci., 15:417–421) and/or through somatic embryogenesis from a well defined root-shoot axis (Vasil et al., 1984, Amer. J. Bot. 71:158–161). The origin of regenerated shoots in Type I callus is not always obvious and appears to take place via sub-epidermal meristem formation (Franz and Schel, 1991, Can. J. Bot. 69:26–33).

Type II callus, which is not as common as Type I, consists of soft, friable, embryogenic cells and can only be generated from certain monocotyledonous genotypes (Phillips et al, 1988, In, Corn and Corn Improvement, pp 345–387). It grows rapidly, contains little or no vascular elements and can be described as friable, embryogenic callus (U.S. Pat. No. 5,641,664 to Plant Genetics Systems). A distinguishing feature of Type II callus is that it contains numerous globular somatic embryos attached to suspensor-like structures on its surface through which plant regeneration appears to progress in clearly identifiable stages (Franz, 1988, Ph.D. Thesis, University of Wageningen, The Netherlands).

Type III callus has only been most recently described. Said callus is formed only very rarely, is easily dispersed in liquid and does not have any distinct somatic embryos on its surface. It has also been described as "friable, non-mucilaginous" callus (Shillito et al., 1989, Bio/Technology 7:581–587) and consists predominately of undifferentiated tissues capable of regeneration via somatic embryogenesis. Type III callus is considered the ideal tissue for transformation and regeneration because cells thereof easily disassociate and disperse, and thus, readily form suspension cultures. This type of callus is most rare, distinct from Type II callus, and can only be produced by visually selecting and preferentially enriching for it at each sub-culture passage of Type II cultures (WO94/28148; Zeneca).

In cotton, as with other dicotyledonous plants, callus types are typically not defined as Type I, II, or III. Moreover, hypocotyl- and cotyledon-derived callus cultures from cotton have been classified into non-embryogenic and embryogenic depending on morphology and regenerative capacity (Shoemaker et al., 1986 Plant Cell Rep. 3:178–181). Non-embryogenic callus is comprised of a loose, friable mass of cells that does not exhibit a strong cytoplasm staining reaction and cannot be used to readily regenerate plants. However, embryogenic callus appears as a tightly compact, dense cytoplasmic mass of cells capable of plant regeneration via somatic embryogenesis. Somatic embryos produced therefrom first appear as globular structures which gradually elongate and then begin to exhibit cotyledonary development.

Of the callus types disclosed herein, Type I and Type II callus cultures derived from monocotyledonous plants are preferred in the production and regeneration of plants. Transgenic maize plants generated via whisker-mediated transformation are most preferably made from either Type I or Type II cultures; whereas, Type I callus cultures are most preferred in the production and regeneration of transgenic rice plants. In addition, cotyledonary node derived and hypocotyl-derived cultures are preferred in the production of transgenic cotton plants, with cultures produced from cotyledon tissue being most preferred.

Shoot tips of plants, including maize, rice, and cotton, contain apical meristems where organ primordia form from apical initial and subepidermal cells (Steeves and Sussex, 1989, Patterns in Plant Development, Cambridge University Press). Meristems can be isolated, placed onto shoot multiplication medium, and induced to produce multiple shoots from which plants can be regenerated (Zhong et al., 1992, Planta 187:483–489). Meristems, either freshly isolated or precultured to initiate shoot multiplication, can serve as recipient tissues for whisker-mediated transformation as taught in the present invention. Shoot tips containing meristematic regions are preferably removed from developing embryos (Lowe et al., 1995, Bio/Technology 13:677–682) or germinating seedlings (Gould et al., 1991, Plant Physiol. 95:426–434), transformed using whiskers with or without an osmotic pretreatment, and placed onto shoot proliferation medium containing a selection agent prior to plant regeneration (Zhong et al., 1996, Plant Physiol. 110:1097–1107).

The heterologous DNA used for transformation herein may be circular, linear, double-stranded or single-stranded. Generally, said DNA is a recombinant vector plasmid and contains coding regions therein which serve to promote expression of the heterologous gene of interest as well as provide a selectable marker whereby those tissues containing said gene can be identified. Preferably, these recombinant vectors are capable of stable integration into the plant genome where selection of transformed plant lines is made possible by having said selectable marker expression driven either by constitutive, tissue-specific, or inducible promoters included therein.

One variable present in a heterologous DNA is the choice of the chimeric gene. Chimeric genes, either in the sense or antisense orientation, are expressed in plant cells under control of a constitutive, tissue-specific, developmental, or inducible promoter and the like. Preference for a particular chimeric gene is at the discretion of the artisan; however, chimeric genes can be, but are not limited to, from plants, animals, or bacteria and the like and can used to express proteins either not found in a non-transformed cell or found in a transformed cell. Chimeric genes can be also used for, but are not limited to, up-regulation or down-regulation of an endogenous gene of interest.

Another variable is the choice of a selectable marker. Preference for a particular marker is at the discretion of the artisan, but any of the following selectable markers may be used along with any other gene not listed herein which could function as a selectable marker. Such selectable markers include but are not limited to aminoglycoside phosphotransferase gene of transposon Tn5 (Aph II) which encodes resistance to the antibiotics kanamycin, neomycin and G418, as well as those genes which encode for resistance or tolerance to glyphosate; hygromycin; methotrexate; phosphinothricin (bialophos); imidazolinones, sulfonylureas and triazolopyrimidine herbicides, such as chlorsulfuron; bromoxynil, dalapon and the like.

In addition to a selectable marker, it may be desirous to use a reporter gene. In some instances a reporter gene may be used with or without a selectable marker. Reporter genes are genes which are typically not present in the recipient organism or tissue and typically encode for proteins resulting in some phenotypic change or enzymatic property. Examples of such genes are provided in K. Weising et al. Ann. Rev. Genetics, 22, 421 (1988), which is incorporated herein by reference. Preferred reporter genes include the beta-glucuronidase (GUS) of the uidA locus of *E. coli*, the chloramphenicol acetyl transferase gene from Tn9 of *E. coli*, the green fluorescent protein from the bioluminescent jellyfish *Aequorea victoria*, and the luciferase genes from firefly *Photinus pyralis*. An assay for detecting reporter gene expression may then be performed at a suitable time after said gene has been introduced into recipient cells. A preferred such assay entails the use of the gene encoding beta-glucuronidase (GUS) of the uida locus of *E. coli* as described by Jefferson et al., (1987 Biochem. Soc. Trans. 15, 17–19) to identify transformed cells.

Another variable is a promoter regulatory element. In addition to plant promoter regulatory elements, promoter regulatory elements from a variety of sources can be used efficiently in plant cells to express heterologous genes. For example, promoter regulatory elements of bacterial origin, such as the octopine synthase promoter, the nopaline synthase promoter, the mannopine synthase promoter; promoters of viral origin, such as the cauliflower mosaic virus (35S and 19S), 35T (which is a re-engineered 35S promoter, see PCT/US96/1682; WO 97/13402 published Apr. 17, 1997) and the like may be used. Plant promoter regulatory elements include but are not limited to ribulose-1,6-bisphosphate (RUBP) carboxylase small subunit (ssu), beta-conglycinin promoter, phaseolin promoter, ADH promoter, heat-shock promoters and tissue specific promoters.

Other elements such as matrix attachment regions, scaffold attachment regions, introns, enhancers, polyadenylation sequences and the like may be present and thus may improve the transcription efficiency or DNA integration. Such elements may or may not be necessary for DNA function, although they can provide better expression or functioning of the DNA by affecting transcription, stability of the mRNA and the like. Such elements may be included in the DNA as desired to obtain optimal performance of the transformed DNA in the plant. Typical elements include but are not limited to Adh-intron 1, the alfalfa mosaic virus coat protein leader sequence, the maize streak virus coat protein leader sequence, as well as others available to a skilled artisan.

Constitutive promoter regulatory elements may also be used thereby directing continuous gene expression in all cells types and at all times (e.g., actin, ubiquitin, CaMV 35S, and the like). Tissue specific promoter regulatory elements are responsible for gene expression in specific cell or tissue types, such as the leaves or seeds (e.g., zein, oleosin, napin, ACP, globulin and the like) and may also be used.

Promoter regulatory elements may also be active during a certain stage of the plants' development as well as active in specific plant tissues and organs. Examples of such include but are not limited to pollen-specific, embryo specific, corn silk specific, cotton fiber specific, root specific, seed endosperm specific promoter regulatory elements and the like. Under certain circumstances it may be desirable to use an inducible promoter regulatory element responsible for expression of genes in response to a specific signal, such as: physical stimulus (heat shock genes); light (RUBP carboxylase); hormone (Em); metabolites; and stress. Other desirable transcription and translation elements functional in plants may also be used. Numerous plant-specific gene transfer vectors are known and available to the skilled artisan.

Heterologous DNA can be introduced into regenerable plant cell cultures via whiskers-mediated transformation. While a general description of the process can be found in U.S. Pat. Nos. 5,302,523 and 5,464,765, both to Zeneca, no protocols have been published to date for whisker-mediated transformation of Type I, Type II, hypocotyl or cotyledon regenerable plant cell lines.

In whisker-mediated transformation, DNA uptake into plant material is facilitated by very small, elongated, needle-like particles comprised of a biologically inert material. When said particles are agitated in the presence of DNA and plant cell lines, one or more of the particles produce small punctures in the regenerable plant cell aggregates thereby allowing said aggregates to uptake the DNA. Cells which have taken up the DNA are considered to be transformed. Some transformed cells stably retain the introduced DNA and express it.

The elongated needle-like particles used in plant cell transformation are termed "whiskers" and are preferably made of a high density material such as silicon carbide or silicon nitride; however, any material having a needle-like structure wherein the size of said structure is smaller than the cell intended to be transformed is within the scope of the invention. More preferably, whiskers are made of silicon carbide and are either Silar SC-9 or Alfa Aesar as described herein.

Before transformation, plant cell lines are preferably placed onto anosmotic medium and allowed to incubate thereby enhancing transformation over non-osmotically treated cells. Most preferred is an osmotic medium having therein about 36.4 g/L sorbitol and about 36.4 g/L mannitol. These tissue are maintained on said medium for about 4 h before whisker-mediated transformation. Incubation on medium with osmoticum after transformation at the discretion of the artisan. However, transformation of non-osmotically treated plant cells aggregates and tissues is also within the scope of this invention.

Callus cultures used herein for generation of transgenic plants should generally be about 3 weeks to about 20 weeks old depending on the culture type. Typically, callus should be about midway between transfer periods and thus beyond any lag phase that might be associated with transfer to a new media or before reaching any stationary phase typically associated with a culture being on a plate for an extended period of time. However, plant material can be taken before or after sub-culturing; therefore, harvest timing is not generally believed to be critical to practicing the invention as disclosed herein. The amount of callus tissue used in each transformation can vary with amounts of about 100 mg to about 500 mg preferred, about 100 mg to about 250 mg being more preferred and about 200 mg tissue being most preferred.

For transformation, whiskers are typically placed in a small container, such as a conical or microfuge tube and the like, wherein is placed a mixture comprising the DNA construct of interest, a liquid medium, and callus tissue. The order in which materials are added is not significant to practicing the invention as disclosed herein. Thereafter, the container is sealed and agitated. Unlike particles used in biolistic transformation of plant tissue (Sanford et al., 1990 Physiol. Plantarum, 79:206–209; and U.S. Pat. No. 5,100, 712), whiskers do not require any special pretreatment with DNA carriers or precipitants prior to use such as $CaCl_2$, spermidine, sheared salmon sperm DNA and the like.

Agitation time used in the transformation process can vary and is typically from between about 10 sec to about 160 sec. The amount of whiskers added per transformation can also vary from between about 1 mg to about 4 mg per tube. An inverse relationship is observed between the amount of whiskers added and the agitation time needed to obtain optimal transformation. Therefore, the amount of whiskers added and the agitation time needed to achieve transformation is determinable by one having skill in the art. In addition, the volume of liquid medium added can vary from about 200 $\mu$L to about 1000 $\mu$L, with about 200 $\mu$L being preferred. Moreover, the amount of heterologous DNA added can vary from a preferred amount of about 10 $\mu$L to about 100 $\mu$L of 1 mg/mL solution. The volume of DNA added is not as critical of factor to the invention as disclosed herein as the final DNA concentration. However, preferred final DNA concentrations are from about 0.03 $\mu$g/$\mu$L to about 0.14 $\mu$g/$\mu$L. The scope of the present invention is not intended to be limited to said container size, the amount or concentration of heterologous DNA added, the volume of heterologous DNA added, the amount of the liquid medium added, the amount of callus material added or the amount of whiskers added as disclosed herein. The scope of the invention is also not intended to be limited by the instrumentation used to agitate the mixture or whether agitation is accomplished by manual or mechanical means.

Once the plant cell lines have been perforated and the heterologous DNA has entered therein, it is necessary to identify, propagate, and select those cells which not only contain the heterologous DNA of interest but are also capable of regeneration. Said cells and plants regenerated therefrom can be screened for the presence or absence of the heterologous DNA by various standard methods including but not limited to assessment of reporter gene expression. Alternatively, transmission of a selectable marker gene along with or as part of the heterologous DNA allows those cells containing said DNA to be identified by use of a selective agent.

Selection of only those cells containing and expressing the heterologous DNA of interest is a critical step in production of fertile, transgenic plants. Selection conditions must be chosen in such a manner as to allow growth of transformed cells while inhibiting growth of untransformed cells, which initially, are far more abundant. In addition, selection conditions must not be so severe as to cause transformed cells to lose their plant regenerability, future viability or fertility. A skilled artisan can easily determine appropriate conditions for selecting transformed cells expressing a particular selectable marker by performing growth inhibition curves. Growth inhibition curves are generated by plotting cell growth versus selective agent concentration. Typically, selective agent concentrations are set at a concentration whereby almost all non-transformed cells are growth inhibited but yet are not killed. Preferred are selective agent concentrations wherein 90–99% of non-transformed cells are growth inhibited but yet not killed. Most preferred are selective agent concentrations wherein 97–99% of non-transformed cells are growth inhibited but yet not killed.

Transformed callus tissues transferred and exposed to selective agents are generally incubated on solid medium supportive of growth. The medium preferred for each type of tissue has been well defined in the art. After initial exposure to selective agents, tissues are transferred periodically to fresh medium while maintaining selective agent concentrations. After transformed cell mass has essentially doubled in size, masses showing the most growth and appearing to be healthy are selected and transferred to fresh medium having selective agent concentrations wherein non-transformed cells will be killed. Repeated selection and transference of growing cells to fresh medium result eventually in a selected group of cells comprised almost exclusively of transformed cells containing the heterologous DNA of interest.

Regeneration, while important to the present invention, may be performed in any conventional manner available to the skilled artisan. If cells have been transformed with selectable marker gene, the selective agent may be incorporated into the regeneration media to further confirm that the regenerated plantlets are transformed. After subsequent weeks of culturing, regenerated plantlet immune to the selective agent can be transferred to soil and grown to maturity.

Callus and plant derived therefrom can be identified as transformants by phenotypic and/or genotypic analysis. For example, if an enzyme or protein is encoded by the heterologous DNA, enzymatic or immunological assays specific for the particular enzyme or protein can be used. Other gene products may be assayed by using suitable bioassays or chemical assays. Other techniques include analyzing the genomic component of the plant using methods as described by Southern ((1975) J. Mol. Biol., 98:503–517), polymerase chain reaction (PCR) and the like.

Plants regenerated from transformed callus are referred to as the RO generation or RO plants. Seed produced by various sexual crosses from plants of this generation are referred to as R1 progeny. R1 seed are then germinated to produce R1 plants. Successful transmission and inheritance of heterologous DNA to R1 plants and beyond should be confirmed using the methods described herein.

Generally, the commercial value of transformed corn and progeny thereof will be of greatest value if the heterologous DNA can be incorporated into many different hybrids. This may be achieved by incorporating the heterologous DNA into a large number of parental lines directly as described herein by creating plant cell aggregates of said lines and transforming said lines with whiskers. In addition, this may also be accomplished by crossing initial transgenic fertile plants to normal elite inbred lines and then crossing the progeny thereof back to the normal parent. Progeny from this cross will segregate such that some plants will contain the heterologous DNA of interest and some plants will not. Crossing of lines is continued until the original normal parent has been converted to a genetically modified line containing the heterologous DNA of interest and also possessing essentially all attributes associated with that line originally. Corn breeding techniques needed to accomplish elite germplasm lines and inbreds thereof are well known to the skilled artisan.

Particular embodiments of this invention are further exemplified in the Examples. However, those skilled in the art will readily appreciate that the specific experiments detailed are only illustrative of the invention as described more fully in the claims which follow thereafter.

EXAMPLE 1

ESTABLISHMENT OF TYPE I and TYPE II MAIZE CALLUS TISSUE

For Type I callus initiation, zygotic embryos (1.5–30 3.0 mm) of the genotypes H99, Pa91, and a proprietary line, 139/39 (U.S. Pat. No. 5,306,864), were aseptically isolated, infra., and placed onto Type I medium consisting of N6 macro-nutrients and vitamins (Chu, 1978, Proc. Symp. Plant Tissue Culture, pp. 43–56), B5 micro-nutrients (Gamborg et al., Exp. Cell Res. 50:151–158), 30 g/L sucrose, 2.9 g/L L-proline, 100 mg/L myo-inositol, 100 mg/L casein hydrolysate, 37 mg/L sodium salt of Ferrous-ethylenediaaminetetraacetic acid (NaFeEDTA), 8 mg/L dicamba, 0.8 mg/L 2,4-D, 4.9 mg/L $AgNO_3$ and 2.5 g/L GELRITE. Type I callus, initiated from the scutellar region of the original zygotic embryo, consisted of compact embryogenic tissue exhibiting scutellar-like structures and shoot meristems. After several passages of selective subculturing at 21–28 day intervals, the cultures were used for transformation experiments described herein.

For Type II callus initiation, plants of a hybrid made by inter-mating two $S_3$ lines derived from a B73×A188 cross (Armstrong et al., 1991, Maize Genet. Coop. News Lett., 65:92–93) were grown under standard greenhouse conditions and self- or sib-pollinated (Petolino and Genovesi, 1994, The Maize Handbook, pp. 701–704). Ten to 14 days after pollination (DAP), developing ears were removed and surface sterilized with 70% (v/v) ethanol for 2 min followed by soaking in 20% (v/v) commercial bleach for 0.5 h containing a few drops of LIQUI-NOX, then rinsed several times with sterile $H_2O$. Immature embryos (1.5–3.0 mm) were then isolated and placed onto initiation medium [N6 basal salts and vitamins (Chu, 1978, Proc. Symp. Plant Tissue Culture, pp. 43–56), 20 g/L sucrose, 2.9 g/L L-proline, 100 mg/L enzymatic casein hydrolysate (ECH), 37 mg/L Fe-EDTA, 10 mg/L $AgNO_3$, 1 mg/L 2,4-dichlorophenoxyacetic acid (2,4-D), and 2.5 g/L GELRITE (Schweizerhall, South Plainfield, NJ) at pH 5.8]. After 2–3 weeks in the dark at 28° C., Type II callus with numerous globular and elongated somatic embryos was obtained. An additional 2–3 selective subcultures were performed to enrich Type II cultures with desirable morphology as described in Welter et al., 1995, Plant Cell Rep. 14:725–729. Once Type II morphology was established (4–6 weeks), callus was transferred to maintenance medium (initiation medium containing 6 mM L-proline and no $AgNO_3$). Type II callus was used for transformation after about 16–20 weeks from culture initiation.

EXAMPLE 2

CONSTRUCTION OF THE PLASMID pUGN81-3 AND pDAB418

The maize expression vector, pUGN81-3, containing the ubiquitin promoter regulatory element driving the β-glucuronidase gene was used as disclosed herein. Plasmid pUGN81-3 was a 8730 base pairs double stranded plant transformation vector composed of the following sequences in clockwise order. Nucleotides 1 to 17 encoded a polylinker. Nucleotides 18 to 2003 of pUGN81-3 were the maize ubiquitin promoter and first intron thereof and were PCR amplified from genomic DNA of maize genotype B73 (Christensen et al., (1992) Plant Mol. Biol. 18:675–689). Nucleotides 2004 to 2022 of pUGN81-3 encoded a polylinker Nucleotides 2023 to 4154 of pUGN81-3 corresponded to nucleotides 2551 to 4682 of plasmid pEI101 (Clontech, Palo Alto, Calif.) followed by a 43 nucleotide polylinker. Nucleotides 4265–4776 of pUGN81-3 comprised the double-enhanced 35S promoter, with nucleotides 4265 to 4516 corresponding to nucleotides 7093 to 7344 of the Cauliflower Mosaic Virus genome (Franck et al., (1980) Cell 21:285–294). Nucleotides 4525 to 4776 of pUGN81-3 were a duplication of nucleotides 4265 to 4516 with linker comprising nucleotides 4517 to 4524 between the duplicated sequence. Nucleotides 4777 to 4871 of pUGN81-3 corresponded to bases 7345 through 7439 of the Cauliflower Mosaic Virus genome (Franck et al., (1980) Cell 21:285–294). Nucleotides 4872 to 4891 comprised a linker sequence. Nucleotides 4892 to 5001 of pUGN81-3 corresponded to nucleotides 167 to 277 of the Maize Streak Virus genome with base 187 absent (Mullineaux et al., (1984) EMBO J. 3:3063–3068). Nucleotides 5002 to 5223 corresponded to the modified first intron of the maize alcohol dehydrogenase gene (Adh1-S) (Dennis et al., (1984) Nucleic Acids Res. 12:3983–4000). The modification resulted in removal of 343 nucleotides (bases 1313 to 1656) with bases 1222 to 1312 (intron 5' end) and nucleotides 1657 to 1775 (intron 3' end) of the maize Adh1-S gene remaining. Nucleotides 5224 to 5257 of pUGN81-3 corresponded to Maize Streak Virus (MSV) nucleotides 279 to 312. Both sections of the Maize Streak Virus, hereinafter MSV, sequence comprised the untranslated leader of the MSV coat protein V2 gene, and were interrupted in plasmid pUGN81-3 by the modified Adh1 intron. Nucleotides 5258 to 5814 of plasmid pUGN81-3 corresponded to nucleotides 29 to 585 of the phosphinotricin acetyl transferase (BAR) gene of *Streptomnyces hygroscopicus* (White et al., (1989) Nucleic Acids Res. 18:1062). To facilitate cloning, nucleotides 34 and 575 of the published sequence were changed from A and G to G and A, respectively. This sequence served as the selectable marker. Nucleotides 5815 to 5819 comprised linker. Nucleotides 5820 to 6089 of pUGN81-3 corresponded to nucleotides 4414 to 4683 of plasmid pBI101 (Clontech, Palo Alto, Calif.) followed by linker sequence. The remaining sequence of pUGN81-3 (nucleotides 6095 to 8730) corresponded to the reverse complement of pUC19 (Yanish-Perron et al., (1985) Gene 33:103–119).

The maize expression vector, pDAB418, containied the ubiquitin promoter regulatory element driving the β-glucuronidase gene was used some expression studies. In addition this plasmid carried a second gene which served as a plant selectable marker. Plasmid pDAB418 was a 10,149 base pairs double stranded plant transformation vector included the following sequences in clockwise order. Nucleotides 32 to 2023 of pDAB418 were the maize ubiquitin (Ubi1) promoter and first intron, and were PCR amplified from genomic DNA of maize genotype B73 (Christensen et al., (1992) Plant Mol. Biol. 18:675–689). Nucleotides 2024 to 2042 of pDAB418 comprised linker sequence. Nucleotides 2043 to 3894 of pDAB418 corresponded to nucleotides 2551 to 4402 of plasmid pBI101 (Clontech, Palo Alto, Calif.) followed by linker sequence (bases 3895 to 3904). Nucleotides 3905 to 4174 OF PDAB418 corresponded to 4414 to 4683 of pBI101. Nucleotides 4175 to 4192 were composed of linker sequence. Base 4193 through 6184 was composed of a second copy of the maize ubiquitin promoter and first intron as describe above. This sequence was followed by linker sequence (6185 to 6196). Nucleotides 6197 to 6753 of plasmid pDAB418 corresponded to nucleotides 29 to 585 of the phosphinotricin acetyl transferase (BAR) gene of *Streptomyces* hygroscopicus (White et al., (1989) Nucleic Acids Res. 18:1062). To facilitate cloning, nucleotides 34 and 575 of the published sequence were changed from A and G to G to A, respectively. This sequence served as the selectable marker and was regulated by the maize ubiquitin promoter. Nucleotides 6754 to 6758 were composed of linker. Nucleotides 6759 through 7472 functioned as the 3' polyadenylation sequence and includes bases 21728 through 22441 from the *Agrobacterium tumefaciens* octopine Ti plasmid pTi15955 (Barker et al. (1983) Plant Mol. Biol. 2, 335–350. Sequence 7473 through 7504 was composed of polylinker. The remaining sequence of pDAB418 (nucleotides 7505 to 10149) corresponded to the reverse complement of nucleotides from the plasmid backbone derived from pUC19 (Yanish-Perron et al., (1985) Gene 33:103–119).

EXAMPLE 3

WHISKERS PREPARATION, OPTIMIZATION, AND TYPE I CORN CALLUS TRANSFORMATION

Type I callus was produced from different inbred lines. For testing, about 250 mg samples of each Type 1 callus was placed into 2.0 mL microfuge tubes (Brinkman Instuments, Inc., Westbury, N.Y.), 300 mL of Type I medium consisting of N6 macro-nutrients and vitamins (Chu, 1978, Proc. Symp. Plant Tissue Culture, pp. 43–56), B5 micro-nutrients (Gamborg et al., Exp. Ce. Res. 50:151–158), 30 g/L sucrose, 2.9 g/L L-proline, 100 mg/L myo-inositol, 100 mg/L casein hydrolysate, 37 mg/L NaFeEDTA, 8 mg/L dicamba, 0.8 mg/L 2,4-D, 4.9 mg/L AgNO$_3$], 20 µL of DNA solution [1.0 mg/mL pDAB418 in 10 mM Tris, 1 mM EDTA, pH 8.0], and 200 µL of a 40 µg/µL (SC-9) whisker suspension was added. Each tube was then agitated for 20 sec using a Vortex-Genie 2™ and the callus was transferred back to Type I medium solidified with 2.5 g/L GELRITE and allowed to incubate for 16 h. Afterwards, callus was assayed for GUS expression as described, infra., with results summarized in Table 1.

TABLE 1

GUS expressian in Type I callus.

| Genotype | GUS Expression Units per Sample |
|---|---|
| H99 | 31 ± 26 |
| Pa91 | 22 ± 8 |
| 139/39 | 3 ± 3 |

Transient GUS expression in Type I callus following whisker treatment was observed in all genotypes tested.

EXAMPLE 4

WHISKERS PREPARATION, OPTIMIZATION, AND TYPE II CORN CALLUS TRANSFORMATION

A sterilized suspension of silicon carbide whiskers was prepared by taking about 40 mg of dry whiskers (Silar SC-9 from Advanced Composite Materials Corp., Greer, S.C.; Alfa Aesar from Johnson-Matthey, Ward Hill, Mass.) and placing them into a pre-weighed 2.0 mL polypropylene tube. The tube was then re-weighed to determine the amount of whiskers added, followed by autoclaving. Immediately before use, a 40 mg/mL whisker suspension was made by adding maintenance medium, supra., and vortexing at high speed for 1 min.

In the transformation experiments, either 200 or 500 mg samples of Type II callus from different immature embryo-derived lines were placed into 17×100 mm culture tubes (Falcon 2059, Becton Dickinson, Lincoln Park, N.J.). Into each was added 500 µL of liquid maintenance medium [minus GELRITE], 80 µL of DNA solution [0.5 µg/µL pDAB418 in 10 mM Tris, 1 mM EDTA, pH 8.0], and 50 µL of a 40 mg/mL (SC-9) whisker suspension. Each tube was then agitated for 20 sec using a Vortex-Genie 2™ (Scientific Industries, Bohemia, N.Y.). Negative control experiments were also performed. In one case, callus tissue was treated with whiskers in the absence of DNA. In the other cases, callus tissue was treated with DNA in the absence of whiskers. Regardless of the treatment, callus was then transferred back to solid maintenance medium having 2.5 g/L GELRITE and allowed to incubate for 16 h in the dark at 28° C. Afterwards, callus was placed into GUS assay solution [0.2 M sodium phosphate pH 8.0, 0.1 mM each of potassium ferricyanide and potassium ferrocyanide, 1.0 M sodium EDTA, 0.5 mg/mL 5-bromo-4-chloro-3-indolyl-β-D-glucuronide, and 0.6% v/v Triton x-100]. GUS expression, defined as counts of blue sectors per sample, was measured after 48 h of incubation at 37° C. in the dark and is summarized in Table 2.

TABLE 2

GUS expression following whisker-mediated transformation of callus at a fixed DNA concentration (0.0635 µg/µL Final concentration)

| Callus Amount/tube | GUS Expression Units Per Sample |
|---|---|
| 200 mg callus + whiskers + DNA | 79 ± 22 |
| 200 mg callus + whiskers − DNA | 0 |
| 200 mg callus − whiskers + DNA | 0 |
| 500 mg callus + whiskers + DNA | 51 ± 20 |
| 500 mg callus + whiskers − DNA | 0 |
| 500 mg callus − whiskers + DNA | 0 |

GUS expression was only observed when whiskers and DNA were both agitated in the presence of callus. Slightly higher transient GUS expression was observed when 200 mg of callus per tube was used as compared to 500 mg per tube.

To test the effect of different DNA concentrations, about 200 mg samples of Type II callus from different immature embryo-derived lines were placed into a 17×100 mm culture tube (Falcon 2059, Becton Dickinson, Lincoln Park, N.J.). Into each was added 250 μL of liquid maintenance medium, either 10, 25, or 50 μL of DNA (1.0 10 μg/μL pUGN81-3 in 10 mM Tris, 1 mM EDTA, pH 8.0), and 50 μL of a 40 mg/mL (SC-9) whisker suspension. Each tube was then agitated for 20 sec using a Vortex-Genie 2™ (Scientific Industries, Bohemia, N.Y.). The callus was then transferred back to semi-solid maintenance medium and allowed to incubate for 16 h in the dark at 28° C. Afterwards, callus was assayed for GUS expression as previously described with the results shown in Table 3.

TABLE 3

GUS expression following whisker-mediated transformation of 200 mg callus at varied DNA concentrations.

| Final DNA Concentration | GUS Expression Units Per Sample |
|---|---|
| 0.032 μg/μL | 105 ± 73 |
| 0.077 μg/μL | 86 ± 57 |
| 0.143 μg/μL | 96 ± 76 |

As little as 10 μg of DNA per tube (0.032 μg/μL) containing about 200 mg of callus resulted in transient GUS expression. Increasing the amount of DNA did not appear to significantly increase transient GUS expression.

About 500 mg samples of Type II callus representing different immature embryo-derived lines were prepared as described herein and placed into 17×100 mm culture tubes (Falcon 2059, Becton Dickinson, Lincoln Park, N.J.). Into each was added 500 μL of liquid maintenance medium and 50 μL of a DNA solution [0.5 μg/μL pDAB418 in 10 mM Tris, 1 mM EDTA, pH 8.0]. The callus/DNA mixture was then allowed to incubate for 1 h either at room temperature or on ice. Callus was incubated in the absence of DNA as a negative control. Afterwards, 50 μL of a 40 μg/μL (SC-9) whisker suspension was added and vortexed as described herein. The callus was then transferred back to maintenance medium solidified with 2.5 g/L GELRITE and allowed to incubate for 16 h in the dark at 28° C. Afterwards, the callus was assayed for GUS expression as described previously. Results are summarized in Table 4.

TABLE 4

GUS expression following whisker-mediated transformation of callus pre-incubated with DNA for 1 h.

| DNA Incubation | GUS Expression Units Per Sample |
|---|---|
| DNA + callus + whiskers | 70 ± 65 |
| DNA + callus → 1 h(ice) → whiskers | 23 ± 37 |
| DNA + callus → 1 h(RT) → whiskers | 60 ± 27 |

Incubation of callus with DNA before whisker agitation resulted in lower transient GUS expression, especially when the incubation was at room temperature. Best results were observed when DNA was added immediately prior to whisker treatment.

About 200 mg samples of Type II callus representing different immature embryo-derived lines were either placed onto osmotic medium [maintenance medium containing 36.4 g/L sorbitol and 36.4 g/L mannitol] and allowed to incubate for 4 h or maintained on maintenance medium. The callus was then placed into 17×100 mm culture tubes (Falcon 2059, Becton Dickinson, Lincoln Park, N.J.) and into each was added 200 μL of either liquid osmotic medium or liquid maintenance medium, 20 μL of DNA solution [1.0 μg/μL pUGN81-3 in 10 mM Tris, 1 mM EDTA, pH 8.0], and 50 μL of 40 μg/μL (Alfa) whisker suspension. Each tube was then agitated for 20 sec using a Vortex-Genie 2™, callus was transferred back to either osmotic medium or maintenance medium solidified with 2.5 g/L GELRITE and allowed to incubate for 16 h in the dark at 28° C. Callus was then tested for GUS expression as described previously. Results are summarized in Table 5.

TABLE 5

GUS expression of callus tissue having been osmotically treated before and/or after whisker-mediated transformation.

| Osmotic Treatment | GUS Expression Units Per Sample |
|---|---|
| None | 72 ± 19 |
| Before Only | 245 ± 80 |
| After Only | 67 ± 37 |
| Before and After | 222 ± 83 |

Transient GUS expression was highest in those cultures which included an osmotic treatment before whisker agitation.

About 200 mg samples of Type II callus representing different cell lines were placed onto osmotic medium and allowed to incubate for 4 h. The callus was then placed into 17×100 mm culture tubes (Falcon 2059, Becton Dickinson, Lincoln Park, N.J.) and into each was added 200 μL of liquid osmotic medium [minus GELRITE], 20 μL of DNA solution [1.0 mg/mL pUGN81-3 in 10 mM Tris, 1 mM EDTA, pH 8.0] and either 25, 50, or 100 μL of a 40 μg/μl (Alfa) whisker suspension. Each tube was then agitated for either 20- or 60 sec using a Vortex-Genie 2™. The callus was then transferred back to liquid osmotic medium, allowed to incubate for 16 h in the dark at 28° C., and then assayed for GUS expression as described previously. Results are summarized in Table 6.

TABLE 6

GUS expression of callus tissue transformed with various amounts of whiskers for 20- and 60 sec.

| | GUS Expression Units Per Sample | |
|---|---|---|
| Whisker Amount | 20 seconds | 60 seconds |
| 25 μL (1 mg/tube) | 61 ± 36 | 136 ± 80 |
| 50 μL (2 mg/tube) | 70 ± 46 | 183 ± 126 |
| 100 μL (4 mg/tube) | 155 ± 92 | 175 ± 98 |

Averaged over all whisker amounts, highest GUS expression was observed following 60 sec agitation compared to 20 sec. However, a 60 sec agitation appeared to substantially damage the callus. High GUS expression was also observed when 100 μL of the whisker suspension was used (4 mg whiskers/tube). Our data indicate that increased whisker amounts can compensate for agitation time and visa versa. The most preferred conditions was 100 μL of whiskers vortexed for 20 sec.

About 500 mg samples of Type II callus representing different cell lines were placed onto osmotic medium and allowed to incubate for 4 h. The callus was then placed into 17×100 mm culture tubes (Falcon 2059, Becton Dickinson, Lincoln Park, N.J.) and into each was added 1000 μL of liquid osmotic medium, 27.7 μL of DNA solution [0.72

μg/μL pUGN81-3 in 10 mM Tris, 1 mM EDTA, pH 8.0], and 200 μL of 40 μg/kL whisker suspension using either Silar SC-9 (Advanced Composite, Greer, S.C.) or Alfa Aesar (Johnson Matthey, Ward Hill, Mass.) whiskers. Each tube was then agitated for 20 sec using a Vortex-Genie 2™ and the callus was transferred back to osmotic medium solidified with 2.5 g/L GELRITE and allowed to incubate for 16 h at 28° C. Afterwards, callus was assayed for GUS expression as described previously with results summarized in Table 7.

TABLE 7

Comparison of whisker type on transformation.

| Whisker Type | GUS Expression Units per Sample |
|---|---|
| Silar SC-9 | 113 ± 48 |
| Alfa Aesar | 51 ± 9 |

Although both worked, better transient GUS expression was observed using Silar SC-9 whiskers than Alfa Aesar whiskers.

About 500 mg samples of Type II callus representing different cell lines were placed onto osmotic medium and allowed to incubate for 4 h. The callus was then placed into either 17×100 mm culture tubes (Falcon 2059, Becton Dickinson, Lincoln Park, N.J.) or 15 mL conical centrifuge tubes (Corning 25319-15, Corning, N.Y.). Into each was added 1000 μL of liquid osmotic medium, 20 μL of DNA solution [1.0 mg/mL pUGN81-3 in 10 mM Tris, 1 mM EDTA, pH 8.0], and 200 μL of 40 μg/μL (Alfa) whisker suspension. Each tube was then agitated for 20 sec using either a Vortex-Genie or a Caulk Vari-Mix II (Estrada Dental, Rancho Cucamonga, Calif.). Callus was then transferred back to solid osmotic medium, allowed to incubate for 16 h and then assayed for GUS activity (Table 8) as described previously. High levels of transient GUS expression were observed following agitation using both the Vortex and Vari-Mix; however, vortexing appeared to be somewhat better.

TABLE 8

The effect of vessel and agitator type on the transformation of callus tissue with whiskers.

| | GUS Expression Units Per Sample | |
|---|---|---|
| Vessel Type | Vortex | Vari-Mix |
| Falcon | 418 ± 202 | 256 ± 261 |
| Corning | 395 ± 362 | 353 ± 271 |
| Agitator Average | 407 ± 294 | 304 ± 270 |

EXAMPLE 5

PRODUCTION AND REGENERATION OF STABLY TRANSFORMED TRANSGENIC MAIZE PLANTS

About 200 mg sample s of Type II callus w ere placed onto osmotic medium and allowed to incubate for 4 h. The callus was then placed into 17×100 mm culture tubes (Falcon 2059, Becton Dickinson, Lincoln Park, N.J.) and into each was added 200 μL of liquid osmotic medium, 20 mL of DNA solution [1.0 μg/μL pUGN81-3 in 10 mM Tris, 1 mM EDTA, pH 8.0], and 100 μL of 40 μg/μL (Alfa) whisker suspension. Each tube was then agitated for 20 sec using a Vortex-Genie 2™, the callus was transferred back to osmotic medium solidified with 2.5 g/L GELRITE and allowed t o recover for ca. 48 h prior to selection.

The whisker-treated callus was placed onto selection medium [maintenance medium with 30 mg/L Basta™ (Hoechst, Frankfurt, Germany) and no enzymatic casein hydrolysate or L-proline] and transferred to fresh selection medium every four weeks for about 3–4 months. After 10–20 weeks, actively growing colonies were isolated and sub-cultured onto fresh selection medium every two weeks to bulk-up callus prior to regeneration.

For plant regeneration, callus was transferred to induction medium, infra., and incubated at 28° C., 16 h/8 h light/dark photoperiod in low light (13 mE/M$^2$/sec) for one week followed by 28° C., 16 h/8 h light dark photoperiod in high light (40 mE/m$^2$/sec) for one week provided by cool white fluorescent lamps. The induction medium was composed of MS salts and vitamins (Murashige and Skoog, 1962, Physiol. Plant. 15:473–497), 30 g/L sucrose, 100 mg/L myo-inositol, 5 mg/L benzyl amino purine, 0.025 mg/L 2,4-D, 2.5 g/L GELRITE and adjusted to pH 5.7. Following this two-week induction period, callus was transferred to regeneration medium and incubated in high light (40 mE/m$^2$/sec) at 28° C. The regeneration medium was composed of MS salts and vitamins, 30 g/L sucrose, and 2.5 g/L GELRITE adjusted to pH 5.7. The callus was sub-cultured to fresh regeneration medium about every two weeks until plantlets appeared. Both induction and regeneration medium contained 30 mg/L Basta™. Plantlets were transferred to 10 cm pots containing approximately 0.1 kg of dry Metro-Mix 360 (The Scotts Co, Marysville, Ohio), placed in a greenhouse, moistened thoroughly, and covered with clear plastic cups for 2–4 days. At the 3–5 leaf stage, plants were transplanted to 5-gallon pots containing soil and grown to maturity.

EXAMPLE 6

SOUTHERN ANALYSIS OF TRANSFORMED CALLUS AND PLANT TISSUES

BASTA resistant lines were characterized by Southern analysis to confirm the presence of the transgene using a DNA probe specific for the coding region of the gene of interest. DNA from both callus and leaf material was analyzed.

For callus, the material was soaked in distilled water for 30 min. and transferred to a new petri dish prior to lyophilization. Leaf material from plants was harvested at the 6–8 leaf stage. Genomic DNA was prepared from lyophilized tissue as described by Saghai-Maroof et. al. ((1984) Proceed. Nat. Acad. Sci. USA 81:8014–8018). Eight μg of each DNA was digested with the restriction enzyme(s) specific for each plasmid construct using conditions suggested by the manufacturer (Bethesda Research, Gaithersburg, Md.) and separated by electrophoresis on a 0.8% agarose gel. The DNA was then blotted onto nylon membranes as described by Southern ((1975) J. Mol. Biol., 98:503–517). A 1.9 kb DNA probe specific for the GUS coding region was prepared using an Oligolabelling Kit (Pharmacia LKB, Piscataway, N.J.) with 50 mCi of [-$^{32}$P] dCTP (Amersham Life Science, Arlington Heights, Ill.). The radioactive probe was then hybridized to the genomic DNA on the blots in 45 mL of minimal hybridization buffer [10% polyethylene glycol, 7% sodium dodecyl sulfate (SDS), 0.6×SSC where 1×SSC is 0.15 M NaCl, 0.015 M sodium citrate, pH 7.0, 10 mM sodium phosphate, 5 mM EDTA and 100 μg/mL denatured salmon sperm DNA] overnight at 60° C. After hybridization, blots were washed at 60° C. in 0.25×SSC and 0.2% SDS for 45 min., blotted dry and exposed to XAR-5 film (Kodak, Rochester, N.Y.) overnight on two intensifying screens (DuPont, Newark, Del.).

Plants regenerated from transgenic callus lines were tested via Southern analysis and all were found to have the 4.2 kb hybridization product. The hybridizing product was expected to contain the ubiquitin-1 promoter/intron, the GUS coding sequence, and the nos 3' untranslated region. Individual plants regenerated from a given culture all displayed identical hybridization patterns.

EXAMPLE 7

ESTABLISHMENT OF EMBRYOGENIC TYPE I RICE CALLUS TISSUE

For initiation of rice embryogenic Type I callus cultures, mature seeds of a Oryza sativa L. cv. Japonica, Taipei 309, were dehusked and surface-sterilized in 70% (v/v) ethanol for 2–5 min followed by a 30–45 min soak in 50% (v/v) commercial bleach containing a few drops of LIQUI-NOX (Alconox, Inc., New York, N.Y.). The seeds were then rinsed 3 times in sterile $H_2O$ and placed on filter paper before being transferred to induction medium [N6 macro elements (Chu, 1978, Proc. Symp. Plant Tissue Culture, Peking Press, p 43–56), B5 micro elements and vitamins (Gamborg et al., 1968, Exp. Cell Res. 50:151–158), 300 mg/L casein hydrolysate, 500 mg/L L-proline, 500 mg/L L-glutamine, 30 g/L sucrose, 2 mg/L 2,4-D, and 2.5 g/L GELRITE, pH 5.8]. The seeds were cultured on induction medium and incubated in the dark at 28° C. for 3 weeks. Afterwards, emerging primary callus induced from the scutellar region was transferred to fresh induction medium for further maintenance. In general, embryonic callus was selected based on its morphology after each subculture. The general morphology of rice Type I embryogenic callus emerged as hard, compact, nodular structures appearing, and in some cases not appearing, embryo-like. This material was termed Type I.

EXAMPLE 8

WHISKERS PREPARATION, OPTIMIZATION, AND RICE TYPE I CALLUS TRANSFORMATION

Immediately prior to DNA delivery, a sterile 50 µg/µL suspension of silicon carbide whiskers (Silar SC-9) was prepared in water as described previously. About 125–500 mg of Type I rice embryogenic callus being less than 4 months-old was selected and transferred into either a 15 mL Corning conical centrifuge tube or a 1.5 mL microfuge tube to which about 250 µL of liquid initiation medium (initiation medium without GELRITE) had been added. Then, about 10–160 µL of a 50 µg/µL whisker solution was added along with 25 µL of 1 µg/µL pDAB418 DNA solution immediately prior to vortexing for 15–120 sec with Vortex Genie 2™ at the highest speed possible. Afterwards, the callus was transferred to initiation medium with and without high osmoticum [0.2 M mannitol and 0.2 M sorbitol; Vain et al., 1993, Plant Cell Rep. 12:84–88] and incubated in the dark at 28° C. for about 24 h before being examined for GUS activity.

Gus histochemical assays were conducted according to Jefferson et al., (1987, EMBO J 6: 3901–3907) and as described here. Tissues were placed in 24-well microtiter plates (Corning, New York, N.Y.) containing 500 µL of assay buffer per well. The assay buffer consisted of 0.2 M sodium phosphate (pH 8.0), 0.1 mM potassium ferricyanide, 0.1 mM potassium ferrocyanide, 1.0 M sodium EDTA, 1.9 mM 5-bromo-4-chloro-3-indolyl-β-D-glucuronide, and 0.06% triton X-100. The plates were incubated in the dark for 1–2 days at 37° C. before microscopically examining the tissue for expression. Silicon carbide whisker-mediated DNA delivery was measured in terms of GUS transient expression, i.e., GUS expression units (blue spots) per sample.

Many different transformation parameters were tested to determine the optimum conditions needed for transformation. Some of the parameters tested included: vortexing time, amount of the 50 µg/µL whisker solution added, treatment with high osmoticum before and/or after whisker treatment, amount of tissue used per transformation, and vessel size. In all of these experiments, the protocols described herein were essentially the same unless otherwise mentioned.

the effect of vortexing time (15–60 sec) was studied for DNA delivery into rice embryogenic Type I callus. In this experiment, callus was treated with high osmoticum for about 4 h prior to transformation with whiskers and for about 6 h following whisker treatment. Callus was transformed by placing 250 mg of callus into a 15 mL Corning conical centrifuge tube, adding 1000 µL of liquid initiation medium, 25 µL of a 1 µg/µL DNA solution (pDAB418), and 100 µL of a 50 µg/µL whisker solution. Multiple sample sets were vortexed for 15-, 30-, 60- and 120 sec and the results were quantitated as shown in Table 9.

TABLE 9

The effect of vortexing time on the transformation of rice Type I embryogenic callus.

| Vortexing Time (Sec) | Gus Expression Units per Sample |
|---|---|
| 15 | 113.5 |
| 30 | 107.5 |
| 60 | 90.5 |
| 120 | 72.5 |

As can be seen, DNA delivery and callus transformation was possible when vortexing for as little as 15 sec despite the hard and compact morphology of rice Type I embryogenic The effect of varying the amount of whiskers added was examined while maintaining a constant volume (1000 µL) of liquid initiation medium. Callus samples were treated with hegh osmoticum before and after whisker-mediated transformation. About 250 mg of callus tissue was selectd and transferred to a 15 mL Corning conical centrifuge tube to which 1,000 µL of liquid initiation medium lacking GEL-RITE was added. Different amounts of a 50 µg/µL whisker solution (10, 20, 40, 80, and 160 µL) along with 25 µL of a 1 µ/µL DNA solution (pDAB418) were added prior to vortexing with Vortex Genie 2™ for 60 sec. Samples were then transferred back onto the initiation medium with high osmoticum overnight before histochemical GUS assays were performed. The results are described in Table 10. GUS expression was found to correlate with an increasing abundance of whiskers added.

TABLE 10

The effect of increasing the amount of whiskers while maintaining a constant volume of initiation medium.

| Whisker Solution Added (µL) | Gus Expression Units/Sample |
|---|---|
| 10 | 2 |
| 20 | 1 |
| 40 | 9 |
| 80 | 6 |
| 160 | 6.5 |

The effect of high osmoticum on transformation efficiency was studied with the results summarized in Table 11. In this experiment, callus tissue was subjected to either no high osmoticum treatment or high osmoticum treatment after whisker-mediated transformation. About 250 mg of callus tissue was transferred to 1.5 mL microfuge tube. About 250 µL of liquid initiation medium was added followed by 125

μL of 50 μg/μL whisker solution and 25 μL of a μg/μL DNA solution (pDAB418). The samples were vortexed for 60 sec and transferred back onto the initiation medium overnight with or without high osmoticum before GUS assays were conducted.

TABLE 11

The effect of osmoticum treatment after vortexing and vortexing time on transformation and transgene expression of rice Type I embryogenic callus tissue.

| Osmoticum After Transformation | mg Tissue | Vortex Sec. | GUS Expression Units Per Sample |
|---|---|---|---|
| + | 250 | 30 | 48 |
| + | 250 | 60 | 44 |
| + | 500 | 30 | 37 |
| + | 500 | 60 | 44 |
| − | 250 | 30 | 87 |
| − | 250 | 60 | 107 |
| − | 500 | 30 | 96 |
| − | 500 | 60 | 120 |

Callus tissue with no high osmoticum treatment after whisker transformation resulted in higher expression levels compared to that where high osmoticum treatment occurred.

The amount of callus tissue added and vessel size (1.5 mL microfuge tube vs. 2.0 mL microfuge tube) used were studied. In this experiment, 125 or 250 mg of callus tissue were used while maintaining a constant volume of liquid initiation medium, i.e., 250 μL. In all cases, 125 μL of a 50 μg/μL whisker solution along with 25 μL of a 1 μg/μL DNA solution (pDA3418) were added prior to vortexing with Vortex Genie 2™ for 60 sec. Following transformation, callus samples were incubated on the initiation medium with high osmoticum overnight before GUS assays were conducted. The results are summarized in Table 12.

TABLE 12

The effect of vessel size and the amount of tissue added on the whiskers-mediated transformation of rice Type 1 callus tissue.

| mg Tissue | Vessel Size (mL) | Gus Expression Units/Sample |
|---|---|---|
| 125 | 1.5 | 8 |
| 125 | 2.0 | 6 |
| 250 | 1.5 | 24 |
| 250 | 2.0 | 9.5 |

The use of 1.5 mL microfuge tube and 250 mg callus tissue per tube resulted in highest transient expression.

EXAMPLE 9

PLASMID DESCRIPTION FOR pUbiHyg

The rice expression vector, pUbiHyg, contained the maize ubiquitin promoter and first intron from the ubiquitin gene (Ubi1) regulatory element driving the hygromycin 2 phosphotransferase (resistance) gene as described by Gritz and Davies, (1983) Gene 25:179–188. Plasmid pUbiHyg was a 5991 base pairs double stranded plant transformation vector composed of the following sequences in clockwise order. Nucleotides 43 through 2034 of pUbiHyg were the maize ubiquitin promoter and first intron, and were PCR amplified from genomic DNA of maize genotype B73 (Christensen et al., (1992) Plant Mol. Biol. 18:675–689). Nucleotides 2053 through 3078 of pUbiHyg corresponded to nucleotides 211 through 1236 of the the hygromycin B phosphotransferase (resistance) gene sequence (accession number K01193), with bases 2056 and 2057 of pUbiHyg modified from AA to GT to facilitate future cloning. Bases 3079 through 3097 were composed of linker. Bases 3093 through 3351 corresponded to nucleotides 4430 to 4683 of plasmid pBI101 (Clontech, Palo Alto, Calif.). The remaining sequence of pUbiHyg (nucleotides 3352 to 5991) corresponded to nucleotides from the plasmid backbone, (Yanish-Perron et al., (1985) Gene 33:103–119).

EXAMPLE 10

PRODUCTION OF STABLY TRANSFORMED RICE TYPE I CALLUS TISSUE AND REGENERATION OF TRANSGENIC PLANTS

For production of stable rice transgenic plants, rice Type I callus tissue was produced as described herein and subjected to whisker-mediated transformation. Typically, 250 mg of rice Type I callus, with or without high osmoticum treatment for four hours, was added to a 1.5 microfuge tube. Also added were 250 μL of liquid initiation medium, 125 μL of a 50 μg/μL whisker solution, and 25 μL of a 1 μg/μL DNA solution (pDAB 305 and UbiHyg in 1:1 ratio). Vortexing was carried out for 60 sec as described previously to ensure DNA delivery.

Following whisker-mediated DNA delivery, callus was transferred to initiation medium, as described previously, with high osmoticum for 24 h before transfer to selection medium. Selection medium consisted of initiation medium with 30 mg/L hygromycin (CalBiochem-Novabiochem Corporation, La Jolla, Calif.). After 2 weeks, cultures were transferred to fresh selection medium having 50 mg/L hygromycin (Li et al., 1993, Plant Cell Rep. 12: 250–30 255). Placing cultures on selection medium resulted in the formation of compact, white-yellow, embryogenic callus cultures after 30–45 days. These cultures were then transferred to pre-regeneration (PR) medium having 50 mg/L hygromycin and maintained in the dark at 28° C. PR medium consisted of initiation medium with 2 mg/L benzyl aminopurine (BAP), 1 mg/L naphthalene acetic acid (NAA), and 5 mg/L abscisic acid (ABA). After 2 weeks, cultures were then transferred to regeneration (RN) medium wherein RN medium was initiation medium with 3 mg/L BAP, and 0.5 mg/L NAA. Cultures on RN medium were incubated for at 28° C. under high fluorescent lights (325-ft-candles) until plantlets emerged. When the plantlet shoots reached about 2 cm, they were transferred to Magenta GA7 boxes (Magenta Corp., Chicago, Ill.) containing medium consisting of MS macro and micro nutrients along with 25 vitamins (Gamborg et al., 1968, Exp. Cell Res. 50:151–158) which had been diluted 1:1 with water, 10 g/L sucrose, 0.05 mg/L NAA, 50 mg/L hygromycin, 2.5 g/L GELRITE, and adjusted to pH 5.8. When plantlets were established with well-developed root systems, they were transferred to soil/metromix 360 (1:1) and raised in the greenhouse (29°/24° C. day/night cycle, 50–60% humidity, 12 h photoperiod) until maturity. Southern analysis of these plants revealed the presence of the hygromycin gene indicating that they were indeed transformed. These plants were successfully grown to maturity in the greenhouse.

EXAMPLE 11

PLASMID DESCRIPTION FOR pSMGN179-3

The expression vector, pSMGN179-3, contained a modified derivative of the chimeric regulatory regions from the *Agrobacterium tumefaciens* opine synthase genes described by Gelvin and Hauptmann, (1995) Patent WO 95/14098 driving the β-glucuronidase gene. Plasmid pSMGN179-3 was a 5541 base pairs double stranded plant transformation vector composed of the following sequences in clockwise order: nucleotides 1 to 16 had the multiple cloning sequence from the plasmid backbone, pUC19 (Yanish-Perron et al., (1985) Gene 33:103–119) Nucleotides 17 to 57 of pSMGN179-3 were composed of linker fragment. Bases 58 through 277 of pSMGN179-3 corresponded to the reverse complement of bases 13774 through 13993 of *Agrobacterium tumefaciens* Ti plasmid pTi15955 T-DNA (Barker et Gal. (1983) Plant Mol. Biol. 2:335–350). These bases corresponded to upstream activating sequences from the octopine synthase (ocs) gene. Bases 278 through 304 corresponded to linker DNA. Bases 305 through 350 corresponded to the reverse complement of bases 21475 through 21520 of *Agrobacterium tumefaciens* Ti plasmid pTi15955 T-DNA (Barker et Gal. (1983) Plant Mol. Biol. 2:335–350). Bases 351 through 737 of pSMGN179-3 were composed of the reverse complement of bases 20128 through 20514 from Agrobacterium b-glucuronidase gene tumefaciens Ti plasmid pTi15955 T-DNA (Barker et Gal. (1983) Plant Mol. Biol. 2:335–350). The sequence of pSMGN179-3 from 305 through 737 included the AMAS promoter described by Gelvin and Haupman, (1995) Patent WO 95/14098. Bases 738 through 763 of pSMGN179-3 contain linker sequence. Bases 58 through 763 of pSMGN179-3 comprised the promoter and untranslated leader regulatory fusion as given in SEQ ID NO 1. Nucleotides 764 to 2615 of pSMGN179-3 corresponded to nucleotides 2551 to 4402 of plasmid pBI101 which encoded the β-glucuronidase gene (Clontech, Palo Alto, Calif.)(Jefferson et al., (1986) Plant Mol. Biol. Rep. 83(22):8447–8451). Bases 767 through 769 were modified from TTA to GTC. The β-glucuronidase gene was followed by polylinker sequence, corresponding to bases 2616 to 2625 of pSMGN179-3. Bases 2626 through 2895 corresponded to 4414 to 4683 of pBI101 which contained the sequence from the nopaline synthase 3' untranslated regions (Clontech, Palo Alto, Calif.)(Jefferson et al., (1986) Plant Mol. Biol. Rep. 83(22):8447–8451). The remaining sequence of pSMGN179-3 (nucleotides 4684 to 5541) corresponded the reverse complement of nucleotides from the plasmid backbone which was derived from pUC19 (Yanish-Perron et al., (1985) Gene 33:103–119).

EXAMPLE 12

TRANSFORMATION OF EMBRYOGENIC COTTON CALLUS

Approximately 250 mg of cotton callus from different seedling-derived lines were placed onto osmotic medium [maintenance medium plus 36.4 g/L sorbitol and 36.4 g/L mannitol] and incubated for 4 h in the dark. The callus was then placed into a 17×100 mm culture tube (Falcon 2059, Becton Dickinson, Lincoln Park, N.J.) into which was added 250 μL of liquid osmotic medium [minus GELRITE], 20 μL of DNA (1.0 μg/μL pSMGN179-3 in 10 mM Tris, 1 mM EDTA, pH 8.0), and 50 μL of a 40 mg/mL (Alfa) whisker suspension. Each tube was then agitated for either 40, 80, or 160 sec using a Vortex-Genie 2™ (Scientific Industries, Bohemia, N.Y.). The callus was then transferred back to osmotic medium solidified with 2.5 g/L GELRITE and allowed to incubate at 28° C. in the dark for 16 h. Afterwards, it was assayed for GUS expression as previously described with the results shown in Table 13.

TABLE 13

GUS expression following whisker-mediated transformation cotton callus using different agitation times.

| Agitation Time | GUS Expression Units Per Sample |
|---|---|
| 40 sec | 41 ± 21 |
| 80 sec | 59 ± 38 |
| 160 sec | 37 ± 28 |

GUS expression was observed in whisker-treated cotton callus. Increasing the agitation time from 40 to 160 sec did not appear to significantly increase expression.

EXAMPLE 13

PLASMID pDAB 305

Plasmid pDAB305 was a 5800 bp plasmid that harbored a promoter containing a tandem copy of the Cauliflower Mosaic Virus 35S enhancer (35S), a deleted version of the Adh1 intron 1, and the untranslated leader from the Maize Streak Mosaic Virus Coat Protein fused to the β-glucuronidase gene, which was then followed by the nos 3'UTR.

What is claimed is:

1. A DNA construct functional in a plant cell comprising in the 5' to 3' direction of transcription, a transcriptional regulatory region functional in said plant cell and having a DNA sequence according to SEQ ID NO:1, and a gene of interest, said gene being either in the sense or antisense orientation.

2. A transcriptional regulatory region comprising the DNA sequence set forth in SEQ ID NO:1.

* * * * *

SEQUENCE LISTING

<160> NUMBER OF SEQ ID NOS: 1

<210> SEQ ID NO 1
<211> LENGTH: 706
<212> TYPE: DNA
<213> ORGANISM: Agrobacterium tumefaciens

<400> SEQUENCE: 1

```
ctacaggcca aattcgctct tagccgtaca atattactca ccggtgcgat gccccccatc      60
gtaggtgaag gtggaaatta atgatccatc ttgagaccac aggcccacaa cagctaccag     120
tttcctcaag ggtccaccaa aaacgtaagc gcttacgtac atggtcgata agaaaaggca     180
atttgtagat gttaacatcc aacgtcgctt tcagggatcc cgaattccaa gcttgggctg     240
```

-continued

```
caggtcaatc ccattgcttt tgaagcagct caacattgat ctctttctcg agggagattt    300
ttcaaatcag tgcgcaagac gtgacgtaag tatccgagtc agtttttatt tttctactaa    360
tttggtcgtt tatttcggcg tgtaggacat ggcaaccggg cctgaatttc gcgggtattc    420
tgtttctatt ccaacttttt cttgatccgc agccattaac gacttttgaa tagatacgct    480
gacacgccaa gcctcgctag tcaaaagtgt accaaacaac gctttacagc aagaacggaa    540
tgcgcgtgac gctcgcggtg acgccatttc gccttttcag aaatggataa atagccttgc    600
ttcctattat atcttcccaa attaccaata cattacacta gcatctgaat ttcataacca    660
atctcgatac accaaatcga ctctagaact agtggatccg tcgacc                   706
```